United States Patent
Alpern et al.

[11] Patent Number: 4,603,427
[45] Date of Patent: Jul. 29, 1986

[54] COLLIMATOR IN A PANORAMIC DENTAL X-RAY APPARATUS

[76] Inventors: Michael C. Alpern, 547 N. Shore Dr., Charlotte Harbor, Fla. 33950; John Kristich, 125 Higgs Dr., NE. Charlotte, Fla. 33952

[21] Appl. No.: 562,020

[22] Filed: Dec. 16, 1983

[51] Int. Cl.$^4$ .......................... G21K 1/04; A61B 6/08; A61B 6/14
[52] U.S. Cl. .................................... 378/150; 378/205; 378/38
[58] Field of Search ................. 370/150, 147, 151–153, 370/205, 206, 38–40; 250/505.1

[56] References Cited

U.S. PATENT DOCUMENTS

| | | | |
|---|---|---|---|
| 3,112,402 | 11/1963 | Okun et al. | 378/147 |
| 3,767,931 | 10/1973 | Williams | 378/206 |
| 4,352,987 | 10/1982 | Hayashi et al. | 378/150 |

FOREIGN PATENT DOCUMENTS

| | | | |
|---|---|---|---|
| 0704187 | 3/1941 | Fed. Rep. of Germany | 378/205 |
| 0345409 | 5/1937 | Italy | 378/153 |
| 0755272 | 8/1980 | U.S.S.R. | 378/39 |

Primary Examiner—Craig E. Church
Assistant Examiner—Charles F. Wieland
Attorney, Agent, or Firm—Banner, Birch, McKie & Beckett

[57] ABSTRACT

A collimator which is adapted to be mounted on the tube head cone of any existing panoramic X-ray machine used in dental examinations. The device personalizes the radiation from an X-ray machine to the size and shape of a patient's head by accurately allowing the X-rays to be directed only to that part of the head which requires the examination. The collimator of our invention comprises a housing which is mounted on the tube head cone of an X-ray machine, the housing having a vertical slot adapted to be aligned with the vertical slot in the X-ray tube head. A vertically-adjustable slide member regulates the open length of the slot in the housing, the slide member being regulated in its position by a pointer which extends from the slide and has an end disposed at a selected part of the patient's head. Thus, the length of the slot in the housing may be regulated to the shape of the patient's head to eliminate radiation to the eyes and retinal tissue, in the upper limit, and under the chin in the lower limit.

16 Claims, 9 Drawing Figures

COLLIMATOR IN A PANORAMIC DENTAL X-RAY APPARATUS

BACKGROUND AND SUMMARY

X-ray examination has been a valuable tool for a doctor to examine an inner part of a patient's body. Orthodontists have found cephalometric and panoramic radiographs, along with all the other diagnostic instruments, to be extremely necessary in order to properly diagnose and treat their patients. However, radiation risks and injury to clinical personnel, as well as to patients, have been a concern of radiographers since the invention of radiographs.

Researchers have found that thyroid damage in the past has been reported due to therapeutic X-ray treatment. These researchers concluded that radiation should be limited to the field of examination because the thyroid gland is susceptible to radiation damage since it is directly in the line of most cephalometric and panoramic radiographs taken by an orthodontist. Study has shown that if the panoramic field in focus is positioned low, excessive thyroid radiation results. On the other hand, if the panoramic field in focus is positioned high, the eye, including the retina and cornea, is unnecessarily radiated.

Our invention makes is possible to limit the panoramic field in focus and this desirable result is accomplished simply, yet effectively. The invention comprises a housing which may be attached to a tube head cone of any one of the existing X-ray devices used in panoramic radiography by orthodontists and dentists in general.

The housing is formed with a vertical slot which is adapted to be aligned with the vertical opening through which the X-rays pass from the tube head. A slide is movably carried by the housing to regulate the panoramic field in focus to include a vertical distance from above the chin of the patient to below the eye of the latter. Thus, the device of our invention has a valuable radiation reduction function, because it personalizes the radiation to the size of the patient by accurately allowing collimation to each individual patient at each individual radiation process.

DESCRIPTION OF THE DRAWINGS

In the drawings accompanying this specification and forming a part of this application, there is shown, for purpose of illustration, an embodiment which our invention may assume, and in these drawings.

DESCRIPTION OF THE PREFERRED EMBODIMENT

Figure 1:
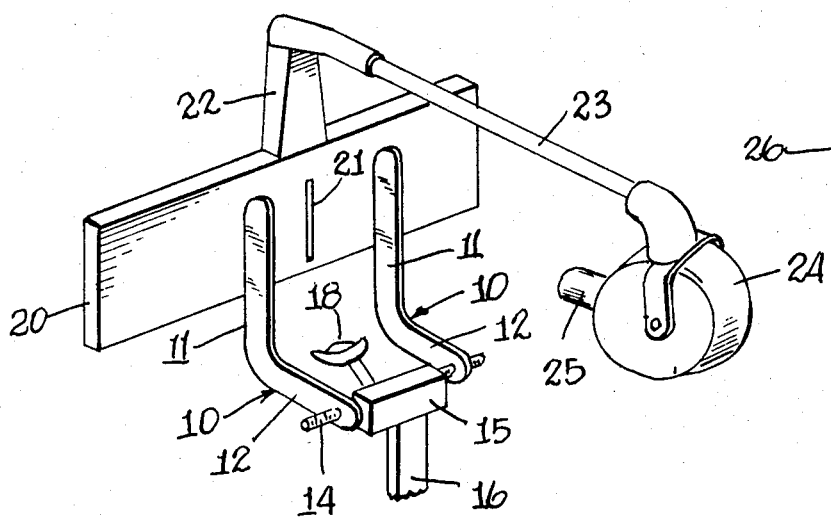
FIG. 1 is a perspective view of apparatus, in use before this invention, for performing panoramic radiography by orthodontists.
Figure 2:
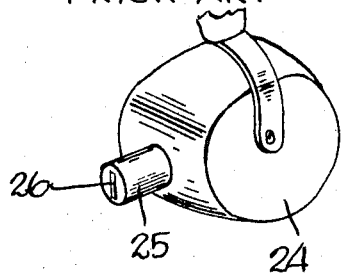
FIG. 2 is a perspective view of the front of the tube head to show the front end of the cone of the apparatus shown in FIG. 1.
Figure 3:
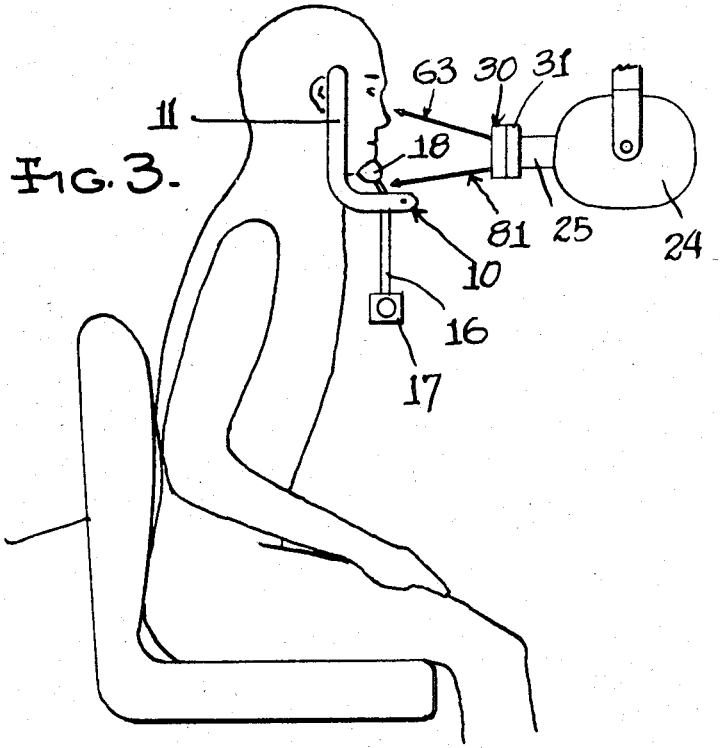
FIG. 3 is a side elevational view of our invention as applied to the tube cone of a radiograph apparatus, showing the pointers which define the vertical extent of the panoramic field in focus, the pointers being shown in operative relation with respect to the head of a patient.

FIG. 1 shows an X-ray machine sold by the S. S. White Company, as representative of the various types of machines available for panoramic radiography. The patient (see FIG. 3) is seated in a chair C and his or her head is held fairly immobile by side bars 10—10 which have vertical components 11—11 adapted to be adjusted laterally to engage the patient's head in vertical alignment with the ear area.

The bars 10 have horizontal components 12—12 carried by a screw-threaded rod 14 extending through a support member 15 which has a depending rigid strap 16 extending downwardly to a body 17 (by means not shown) that is attached to a part of the chair C. A chin rest 18 is rigidly carried by the support member 15. The body 17 is movable vertically relative to the chair C to accomodate the chin rest and the side bars to patients who sit tall or short in the chair.

A film housing 20 is carried by mechanism (not shown but well known) so that it may revolve in a horizontal path around the stationary side bars 10 and chin rest 18, and therefore around the head of the patient which is restrained from movement by the side bars and chin rest. The film housing has an elongated vertical slot 21 about midway of its length, as shown in FIG. 1.

A post 22 extends upwardly from the film housing and has a forwardly-extending arm 23 which carries the head 24 in which the X-ray generator is located. The tube cone 25 extends from the head in a direction toward the film housing and has a vertical slot 26 for passing the X-rays toward the slot 21 in the film housing to energize the film in the housing.

The normal procedure is to seat the patient in the chair C and to adjust the body 17 vertically so that the chin of the patient is comfortably supported in the chin rest 18. The side bars 10—10 are adjusted laterally to confine the patient's head against rotative movement. The vertical position of the body 17 is correlated to the vertical position of the film housing so that if the body 17 is raised or lowered a certain amount, the film housing and tube head 24 should be moved vertically the same amount.

With the patient's head in restrained position, the operator leaves the room and energizes controls which cause the film housing 20 and tube head Z4 to swing in a horizontal path around the patient's head, the X-rays emanating from the slot 26 penetrating the head of the patient and energizing the film in the housing 20 in known manner. Thus, a panoramic picture of the patient's head, in the jaw area, is taken for diagnostic use by the doctor.

As before mentioned, existing panoramic radiographs have no means of collimation to eliminate radiation to the eye and retinal tissue, and the thyroid gland, all of which may be damaged by that radiation. Our invention provides valuable radiation reduction, and comprises a housing 30, formed of a metal such as aluminum which is adapted to be removably attached to the cone 25 of the tube head 24.

Figure 6:
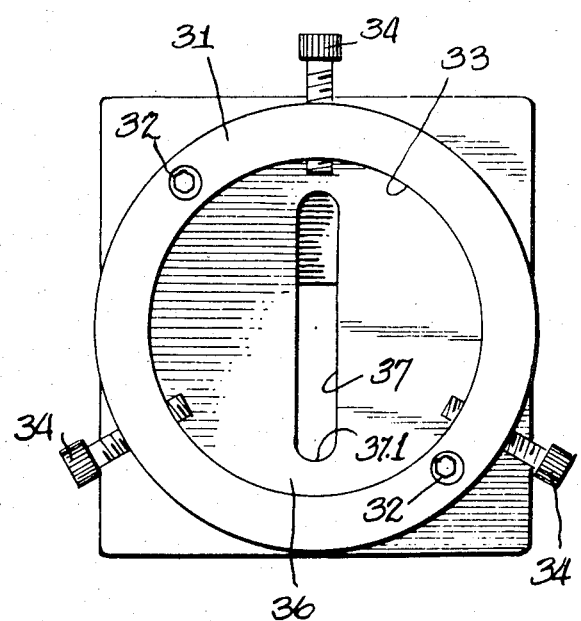
FIG. 6 shows the same housing as viewed from the rear.

A metal ring 31, which may also be formed of aluminum, is attached to the flat rear surface of the housing 30, such as by means of machine screws 32 (FIG. 6). The ring 31 may be round, to provide a round opening 33 to receive a round tube-head cone 25 or may be hexagonal, square or other shape complementary to the shape of the head cone 25 if the latter is other than round. Set screws 34 are threaded through the ring in radial manner to engage peripherally-spaced parts of the cone 25 to firmly hold the housing 30 in position on the cone.

The housing has a vertical opening 35 therethrough, and this opening may be round, as shown best in FIG. 7, or in another shape to accomplish a purpose later to be described. As seen in FIG. 8, the opening 35 leaves a wall 36 therebehind, and this wall is formed with a vertical slot 37 (see also FIG. 6) which opens into the interior of the ring 31 and therefore faces the slot 26 in the tube head cone 25. The round opening 35 communicates with a slot 38 in the front face 39 of the housing 30, one defining wall of the slot 38 having an undercut 41 for a purpose to be described.

A slide plug 42 preferably of stainless steel and of round cross section when the opening 36 is round, is sized to closely but slidably fit within the opening. A side wall of the plug 42 has a flat portion 43 to form spaced heads 44—44 adapted to be engaged by a set screw 45 (FIG. 5) to limit vertical movement of the slide plug 42. A rivet of aluminum or the like is disposed within a side opening 47 (FIG. 5) in the block, and has a head 48 adapted to be pressed against a side wall of slide plug to frictionally hold the latter against free longitudinal movement within the open 35. A coil spring 49 surrounds the shank 50 of the rivet and is compressed between the rivet head 48 and a screw 51 threaded into the side opening 47.

In order to positively hold the slide plug 42 in position, a machine screw 52 which may be formed of brass, is threaded into a side opening 53 (FIG. 5) so that its inner end may be firmly brought into contact with the slide plug. As best seen in FIG. 7, a slot 54 extends longitudinally of and to the front of the slide plug, and a crank arm 55 is disposed within the slot and is of a width to slidably fit between side walls 56—56. The vertical part 57 of the arm is formed with a through opening to pass a pivot pin 58 which also passes through aligned openings 59 in the slide plug to pivotally support the crank arm 55 within the slot 54. The horizontal part of the arm 60 is formed with a threaded opening 61 (FIG. 8) which receives a screw 62 at its rear so that the inclination of the crank arm 55 may be changed, if desired.

The threaded end of a pointer 63 is screwed into the front of the opening 61 or it may be held thereto by force fit or a fused connection. The pointer 63 is formed in telescoping sections, the forward section 64 telescoping into the rear section 65. A round-nosed point 64.1 is carried at the free end of the forward section 64. It should be noted that the pointer 63 is biased to the upwardly-inclined position shown in FIG. 4 by its own weight, but it may be swung upwardly to the out-of-the-way position shown fragmentarily in dot-dash lines in FIG. 4.

Figure 5:
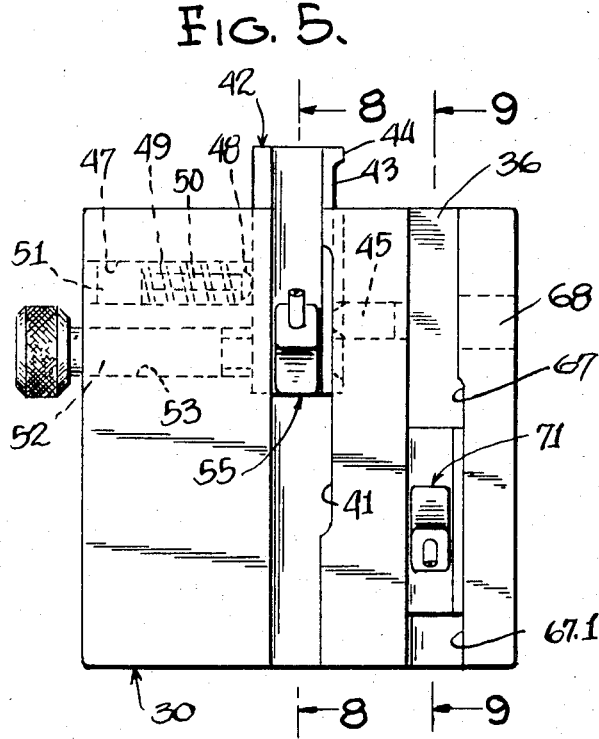
FIG. 5 is a view corresponding to the line 5—5 of FIG. 4, showing the collimator housing as viewed from the front.
Figure 7:
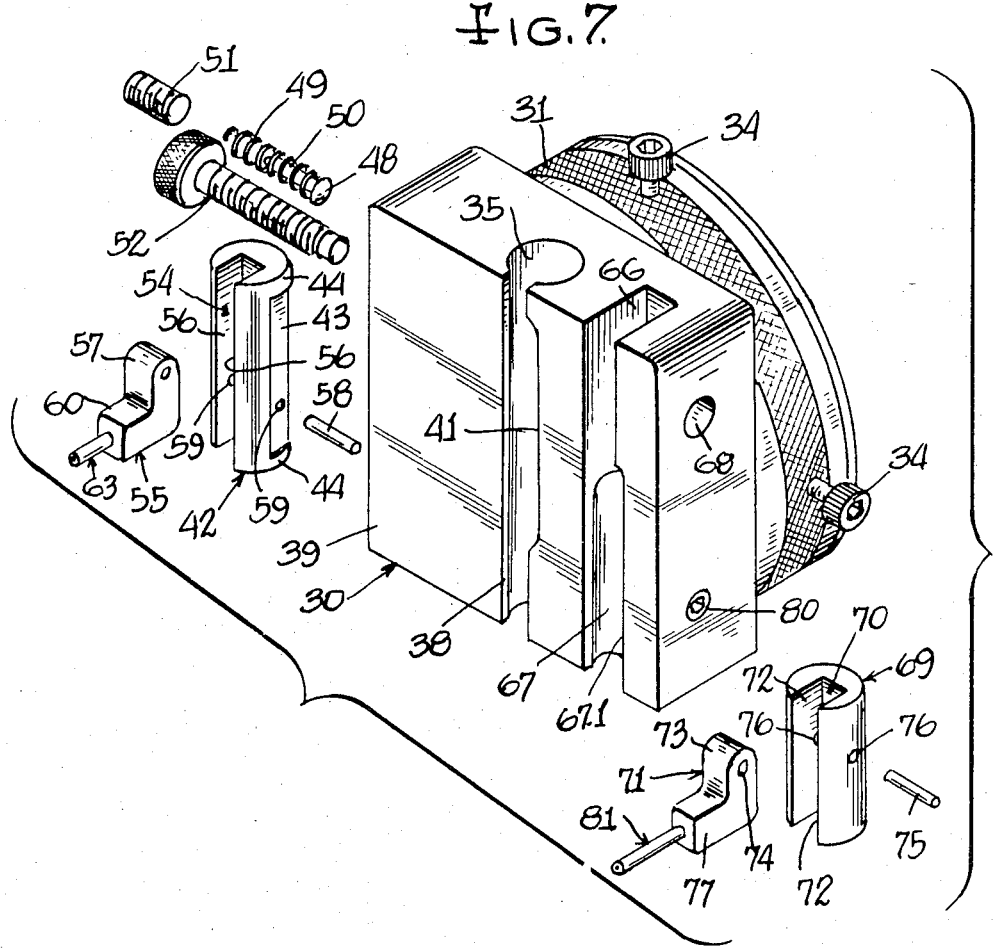
FIG. 7 is a dissassembled perspective view of the parts comprising the collimating device.
Figure 8:
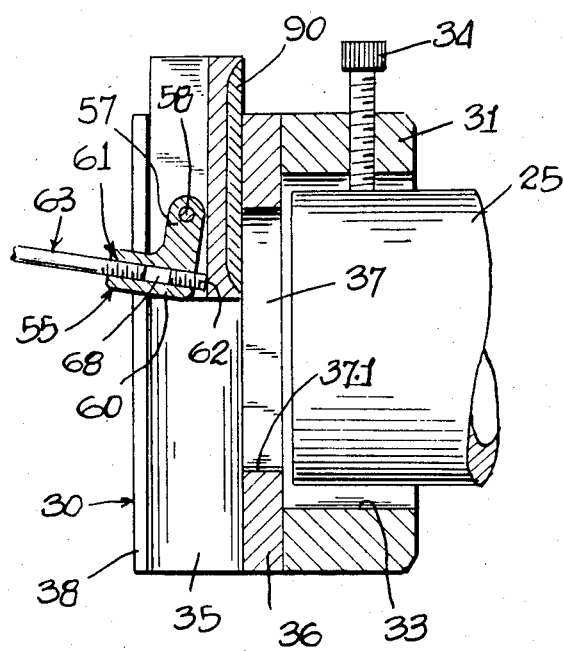
FIGS. 8 and 9 are sectional views corresponding respectively, to the lines 8—8 and 9—9 of FIG. 5.

As best seen in FIGS. 5 and 7, a vertical slot 66 enters the housing 30 from its front surface 39, this slot being positioned to one side of the opening 35. The slot 66 merges with a circular portion 67 at its lower end. The housing has a side opening 68 to pass a tool for threading the set screw 45.

Figure 9:
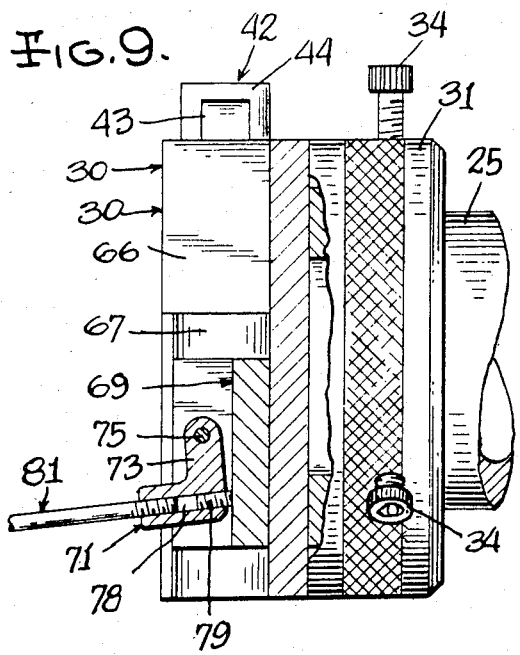

A slide plug 69 snugly but slidably fits within the circular position 67, and this plug has a slot 70 extending longitudinally of and to the front thereof. A crank arm 71 (which may be similar to the arm 55) is of a width to slidably fit between side walls 72 of the slot 70. The vertical part 73 of the arm 71 is formed with a through opening 74 to pass a pivot pin 75 which also passes through aligned openings 76 in the slide plug 69 to pivotally support the crank arm 71 within the slot 70. The horizontal part 77 of the arm 71 is formed with a threaded opening 78 (FIG. 9) which receives a set screw 79 at its rear so that the inclination of the crank arm may be changed, if desired. The slide plug is normally held in a fixed position, once it is in an adjusted relation, by a set screw 80 threaded in a side opening in the housing 30.

The threaded end of a pointer 81 is screwed into the front of the opening 78 or, like the pointer 63, it may be held thereto by a force fit or in a fused connection. The pointer 81 is formed in telescoping sections, the forward section 83 telescoping into the rear section 83. A round-nosed end 84 is carried at the free end of the forward section 82 so that it, and the end 64.1 of the pointer 63, may be safely moved near the head of a patient.

Figure 4:
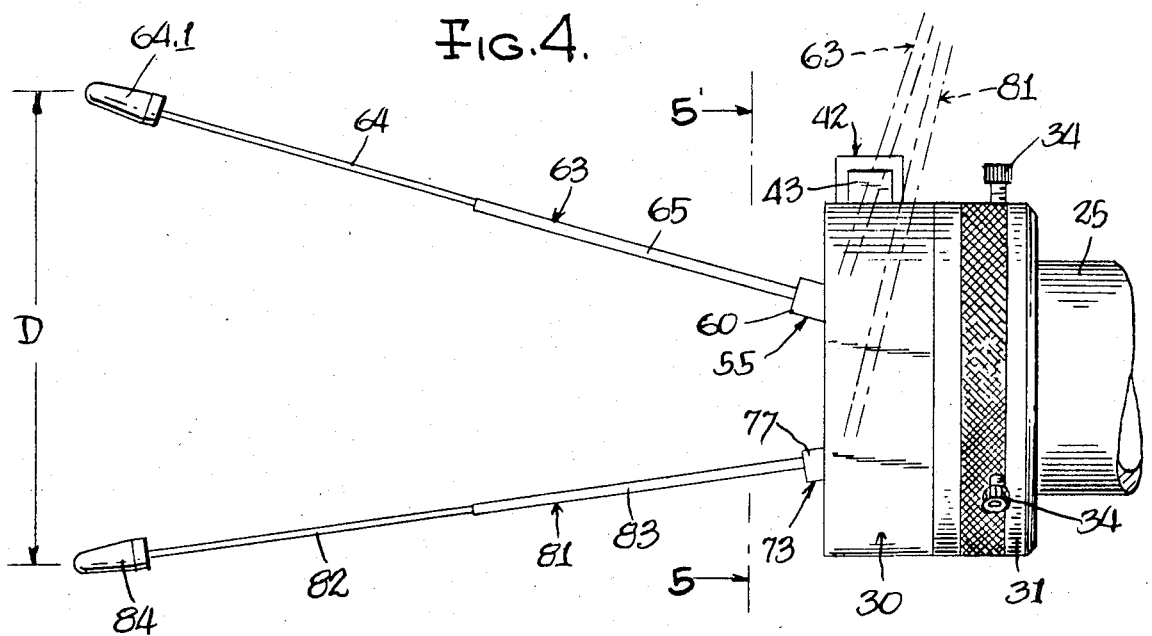
FIG. 4 is an enlarged side view of our collimator as applied to the cone of a tube head, the latter being shown fragmentarily.

It should be noted that the pointer 81 is biased to the downwardly-inclined position shown in FIG. 4 by its own weight, but it may be swung upwardly to an out-of-the-way position shown fragmentarily in dot-dash lines in FIG. 4.

In operation, the collimating device is attached to cone 25 of the tube head 24 of the X-ray machine, by threading the screws 34 through the ring 31 to firm engagement with exterior surface of the cone 25. The patient is seated in the chair C and the body 17 adjusted vertically so that the chin rest 18 comfortably receives the chin of the patient. The side bars 10—10 are then adjusted to comfortably restrain rotation of the patient's head.

The lower pointer 81 is, or has been, adjusted relative tb the lower end 37.1 of the slot 37, so that when its rounded nose 84 is positioned adjacent to but just below the patient's chin, the lower part of the radiation rays do not extend below the patient's chin. The upper pointer 63 is adjusted, by moving the slide plug 42 longitudinally of the opening 35, so that the rounded nose 64.1 is below the eyes of the patient. This will adjust the length of the slot 37 from its bottom end 37.1 upward to the lower end of the slide plug 42, to limit radiation rays to below the eyes of the patient. As best seen in FIG. 8, the rear of the plug 42 may have a recess which is filled with lead 90, to insure limitation of radiation rays to the intended part of the head of a patient.

Once the foregoing adjustments have been made, the pointers 63 and 81 may be swung upward to the dot-dash position shown in FIG. 4, and the X-ray machine energized and the tube head 24 and film housing 20 rotated around the patient's head, causing a continuous picture of the patient to be taken as it revolves.

As suggested in FIGS. 5 and 7, the pointers 63 and 81 may be shifted horizontally a slight amount by reason of the fact that slide plugs 42 and 69 have limited rotative movement in their respective openings 35 and 66, the reliefs 41 and 67.1 in the entrance of such openings permitting rotation of the slide plugs a greater amount in one direction.

In panoramic radiography the X-rays issue from the slot 26 in the tube head cone 25 in a vertical plane, and disperse upward and downward in a fan-shaped sector an amount limited by the length of the slot 37 in the rear wall of the collimator body 30. The distance D in FIG. 4 shows a predetermined vertical length of the X-rays between the nose ends 64.1 and 84. If these ends were adjacent to the patient's head, the distance D would be the length of the patient's head that will be affected by the X-rays.

The lower pointer 81 is adjusted so that it lies along the lowermost part of the X-ray beam, and is then fixed in position. Adjustment of the lower pointer 81 is required because of the difference in various X-ray machines and the slightly different position of the collimator body that may occur by reason of the connection through means of the screws 34.

When the nose 84 of the lower pointer is positioned adjacent to the patient's head, the tube head 24 and film housing are adjusted vertically until the pointer is just below the patient's chin. The upper pointer is then adjusted so that its nose end 64.1 is just below the eyes of the patient, and this causes a change in the length of the slot 37 and a corresponding change in distance D so that the X-rays to the patient are confined to a vertical distance which is below the patient's eye and above the patient's thyroid.

We claim:

1. A collimator in a with panoramic X-ray apparatus in dental examinations, said apparatus including a tube head for housing the X-ray generator and a tube head cone having a vertical slit for passing the X-rays in fan-shape in a vertical plane, said apparatus also including a film housing having a vertical slot aligned with the cone slit to expose the film in said housing to the X-rays emanating from the tube head cone, said apparatus also including means to restrain a patient's head against movement, means to rotate the tube head and film housing in an horizontal orbit around the patient's head, and means to adjust the X-ray apparatus in a vertical direction to align the same to correspond to variations in the size and shape of various patients and their heads, the collimator comprising:

a housing having a vertical slot in a rear wall thereof, and a tubular attachment member attached to said housing to receive and connect to the tube head cone so that the slit in the latter is aligned with the slot in said rear wall, a slide plug mounted in said housing for vertical sliding movement in front of said rear wall slot to regulate the vertical size of the latter and thus the vertical size of the plane of X-rays emanating from the tube head cone, and elongated pointer means carried by said plug to extend forwardly of said housing and toward the patient's head, constructed and arranged to be coincident with the lower end of the plane of X-rays just under the patient's chin, and to determine the vertical position of said slide plug to decrease the length of said rear wall slot from the upper end thereof so that the upper end of the plane of X-rays is below the patient's eyes.

2. The construction according to claim 1 wherein said means extending forwardly of said housing is in the form of a pointer having one end connected to said slide plug and a free end to be positioned adjacent to the patient's head.

3. The construction according to claim 2 wherein said one end of said pointer is pivotally connected to said slide plug, the weight of said pointer urging it to a downward operative position, said pointer being swingable upwardly to an out-of-the-way position.

4. The construction according to claim 3 wherein said pointer is carried by a crank arm, the latter being pivotally connected to said slide plug.

5. The construction according to claim 4 wherein a set screw is carried by said crank arm, adjustment of said set screw adjusting an angular position of said pointer with respect to its forward extension from said housing.

6. The construction according to claim 2 wherein said pointer comprises telescoping sections to compensate for variations in distance between said housing and the patients's head.

7. The construction according to claim 1 wherein said slide plug is frictionally restrained against sliding movement.

8. The construction according to claim 7 and further including a locking screw threaded into said housing and having an inner end to be forcibly engaged with said slide plug.

9. The construction according to claim 1 and further including a second slide plug offset from the first-named slide plug and mounted in said housing for vertical sliding movement.

10. The construction according to claim 9 wherein said means extending forwardly of said housing is in the form of two pointers, one having one end connected to said first-named slide plug and a free end to be positioned adjacent to the patient's head, and the other of said pointers having one end connected to said second slide plug and a free end to be positioned adjacent to the patient's head.

11. The construction according to claim 10 wherein said other of said pointers is to determine vertical adjustment of said X-ray apparatus relative to the patient's head to a position wherein the lower end of the plane of X-rays does not extend low enough to affect the thyroid of the patient, and wherein said one of said pointers is to determine the vertical position of said first-named slide plug so that the upper end of the plane of X-rays does not extend high enough to affect the eyes and retinal tissue of the patient.

12. A collimator for attachment to the tubular head of dental x-ray apparatus comprising:

a housing having means on an inner side facing an x-ray source thereof surrounding the end of said tubular head and detachably securing the housing thereto, said housing having a vertically disposed slot extending through said housing from said inner side to an outer side thereof, said slot being in alignment with said tubular head to pass a planer beam of x-rays therethrough, said housing on the outer side thereof having an elongated vertical groove intersecting said slot, a plug slidably received in said groove between an upper position in which said plug does not obstruct said slot and a lower position in which said plug substantially obstructs said slot, said plug between said upper and lower positions variably obstructing said slot greater and lesser amounts, in order to control the width of said beam of x-rays able to pass through said slot and housing, means frictionally retaining said plug in said groove to prevent unrestrained movement thereof, and, elongated pointer means carried by said plug and extending forwardly of said housing on the outer side thereof for vertically positioning said plug so that the extent of obstruction of said slot is defined with respect to a patient wherein said pointer means is coincident with the lower end of said beam.

13. The collimator of claim 12 further including a second groove in said housing opening to said outer side of said housing, and a second plug slidably mounted in said second groove carrying a second elongated pointer means to facilitate positioning of the patient, said second groove being laterally spaced from said housing slot in non-intersecting relation thereto.

14. The collimator of claim 12 wherein said pointer means is pivotally mounted on said plug to permit angular adjustment thereof relative to said plug, and means for angularly adjusting said pointer means.

15. The collimator of claim 12 wherein said pointed means includes an elongated telescoping rod.

16. The collimator of claim 14 wherein said pointer means is mounted for pivotal movement on said plug to permit swinging thereof to an out-of-the-way position remote from said housing other side when desired.

* * * * *